(12) United States Patent
Zipp et al.

(10) Patent No.: US 12,036,202 B2
(45) Date of Patent: Jul. 16, 2024

(54) ANTIMICROBIAL COMPOSITIONS COMPRISING CANNABINOIDS AND METHODS OF USING THE SAME

(71) Applicant: Graphium Biosciences, Inc., Cleveland, OH (US)

(72) Inventors: Brandon Joel Zipp, Roseville, CA (US); Robert Thomas Brooke, El Segundo, CA (US)

(73) Assignee: GRAPHIUM BIOSCIENCES, INC., Cleveland, OH (US)

( * ) Notice: Subject to any disclaimer, the term of this patent is extended or adjusted under 35 U.S.C. 154(b) by 225 days.

(21) Appl. No.: 17/529,726

(22) Filed: Nov. 18, 2021

(65) Prior Publication Data

US 2022/0071950 A1 Mar. 10, 2022

Related U.S. Application Data

(63) Continuation of application No. 16/612,219, filed as application No. PCT/US2018/031727 on May 9, 2018, now Pat. No. 11,207,291.

(60) Provisional application No. 62/503,417, filed on May 9, 2017.

(51) Int. Cl.
| | |
|---|---|
| A61K 31/352 | (2006.01) |
| A61K 9/00 | (2006.01) |
| A61K 31/05 | (2006.01) |
| A61P 31/04 | (2006.01) |

(52) U.S. Cl.
CPC .......... *A61K 31/352* (2013.01); *A61K 9/0014* (2013.01); *A61K 9/0053* (2013.01); *A61K 31/05* (2013.01); *A61P 31/04* (2018.01)

(58) Field of Classification Search
CPC .... A61K 9/0014; A61K 9/0053; A61K 31/05; A61P 31/04; Y02A 50/30
See application file for complete search history.

(56) References Cited

U.S. PATENT DOCUMENTS

| | | | |
|---|---|---|---|
| 5,292,899 | A | 3/1994 | Tius et al. |
| 5,627,270 | A | 5/1997 | Kahne et al. |
| 8,227,627 | B2 | 7/2012 | Stinchcomb et al. |
| 8,410,064 | B2 | 4/2013 | Radominska-Pandya et al. |
| 8,497,299 | B2 | 7/2013 | Mechoulam et al. |
| 8,858,970 | B2 | 10/2014 | Supamahitorn et al. |
| 9,109,193 | B2 | 8/2015 | Galliher et al. |

(Continued)

FOREIGN PATENT DOCUMENTS

| | | |
|---|---|---|
| KR | 10-1331066 | 11/2013 |
| WO | WO 2009/018389 | 2/2009 |

(Continued)

OTHER PUBLICATIONS

International Search Report and Written Opinion, PCT/US2018/031727, dated Jul. 12, 2018.

(Continued)

*Primary Examiner* — Deborah D Carr
(74) *Attorney, Agent, or Firm* — NORTON ROSE FULBRIGHT US LLP (57) ABSTRACT

The invention relates is directed to antimicrobial compositions comprising cannabinoid compounds and methods of utilizing the antimicrobial compositions to inhibit the growth of microorganisms, to treat and/or prevent microbial infections.

20 Claims, 2 Drawing Sheets

(56) References Cited

U.S. PATENT DOCUMENTS

| | | |
|---|---|---|
| 9,168,276 B2 | 10/2015 | Bombardelli et al. |
| 9,497,299 B2 | 11/2016 | Cai |
| 11,207,414 B2 | 12/2021 | Zipp et al. |
| 2012/0202891 A1 | 8/2012 | Stinchcomb et al. |
| 2014/0298511 A1 | 10/2014 | Lewis et al. |
| 2015/0258040 A1 | 9/2015 | Lynch et al. |
| 2016/0374958 A1 | 12/2016 | Anastassov et al. |
| 2017/0173537 A1 | 6/2017 | Gagnon |
| 2018/0264122 A1 | 9/2018 | Zipp et al. |
| 2019/0382814 A1 | 12/2019 | Peet et al. |
| 2020/0046639 A1 | 2/2020 | Sayre et al. |
| 2023/0346952 A1 | 11/2023 | Hardman et al. |

FOREIGN PATENT DOCUMENTS

| | | | |
|---|---|---|---|
| WO | WO 2009/158499 | 12/2009 | |
| WO | WO 2012/011112 | 1/2012 | |
| WO | WO 2014/108899 | 7/2014 | |
| WO | WO 2014/122227 | 8/2014 | |
| WO | WO 2017/053574 | 3/2017 | |
| WO | WO-2017053574 A1 * | 3/2017 | ........... A61K 31/352 |
| WO | WO 2018/011813 | 1/2018 | |
| WO | WO 2018/176055 | 9/2018 | |
| WO | WO 2020/058509 | 3/2020 | |
| WO | WO 2021/174092 | 9/2021 | |

OTHER PUBLICATIONS

Ali, E.M.M., et al. (2012). "Antimicrobial Activity of Cannabis sativa L." Chinese Medicine. 3:61-64.

Appendino, G., et al. (2008). "Antibacterial Cannabinoids from Cannabis sativa: A Structure-Activity Study." J Nat Prod. 71(8): 1427-1430.

Gigli, S., et al. (2017). "Cannabidiol restores intestinal barrier dysfunction and inhibits the apoptotic process induced by Clostridium difficile toxin A in Caco-2 cells." United European Gastroenterology J. 0(0): 1-8.

Kabelik, J. et al. (1960). "Cannabis as a medicament. UN Office on Drugs and Crime." https://www.unodc.org/unodc/en/data-and-analysis/bulletin/bulletin_1960-01-01_3_page003.html, accessed Aug. 5, 2020.

Van Klingeren, B., Ten Ham, M. (1976). "Antibacterial activity of (delta9)-tetrahydrocannabinol and cannabidiol. Antonie van Leeuwenhoek." 42(1976): 9-12.

CDC, "Antibiotic Resistance Threats in the United States," 2013, 114 pages.

CDC. (2015). "Nearly half a million Americans suffered from Clostridium difficile infections in a single year", https://www.cdc.gov/media/releases/2015/p0225-clostridium-difficile.html, accessed Aug. 5, 2020.

WHO. (2014). Antimicrobial Resistance, Global Report on Surveillance, 256 pages.

WHO. (2017). "Global priority list of antibiotic-resistant bacteria to guide research, discovery, and development of new antibiotics." 7 pages.

Tanaka et al., "Cannabis, 21[1] Biotransformation of Cannabinol to its Glycosides by In Vitro Plant Tissue," *Journal of Natural Products*, Jan. 1, 1993, pp. 2068-2072.

Tanaka et al, "Monoclonal antibody against tetrahydrocannabinolic acid distinguishes Cannabis sative samples from different plant species," *Forensic Science International* 106 (1999) 135-146.

European Search Report for App. No. 16849598.4, dated Apr. 25, 2019.

Tanaka et al., "Cannabis 25[1], Biotransformation of Cannabinol and Cannabidiolic Acid by Pinellia Ternata Tissue Segments," *Plant Cell Reports*, vol. 1, No. 11, Aug. 1, 1996, 819-823.

Tanaka et al., "A New Cannabinoid, Delta6-Tetrahydrocannabinol 2'-O-beta-D-Glucopyranoside, Biotransformed by Plant Tissue," Jan. 1, 1997.

Tanaka, "Immunochemical Approach Using Monoclonal Antibody Against delta9-Tetrahydrocannabinolic Acid (THCA) to Discern Cannabis Plants and to Investigate New Drug Candidates," *Current Drug Discovery Technologies*, vol. 8, No. 1, Jan. 1, 2011, 3-15.

Bartzokis G. (2004). Age-related myelin breakdown: a developmental model of cognitive decline and Alzheimer's disease. Neurobiology of Aging. 25:5-18.

Bisogno T, et al. (2001) Molecular targets for cannabidiol and its synthetic analogues: effect on vanilloid VR1 receptors and on the cellular uptake and enzymatic hydrolysis of anandamide. British Journal of Pharmacology. 134, 845-852.

Chen Q, et al. (2009). Synthesis, in vitro and in vivo characterization of glycosyl derivatives of ibuprofen as novel prodrugs for brain drug delivery. J Drug Targeting. 17(4):318-328.

Conchie J., Findlay J., Levvy GA. (1958). Mammalian Glycosidases, Distribution in the body. Biochem J. 71(2):318-325.

De Petrocellis L, et al. (2011) Effects of cannabinoids and cannabinoid-enriched Cannabis extracts on TRP channels and endocannabinoid metabolic enzymes. British Journal of Pharmacology. 163, 1479-1494.

Friend DR., Chang GW. (1984). A Colon-Specific Drug-Delivery System Based on Drug Glycosides and the Glycosidases of the Colonic Bacteria. J Med Chem. 27:261-266.

Friend DR., Chang GW. (1985). Drug Glycosides: Potential Prodrugs for Colon-Specific Drug Delivery. J Med Chem. 28:51-57.

Gomez O., Arevalo-Martin A., Garcia-Ovejero D., Ortega-Gutierrez S., Cisneros JA., Almazan G, Sanchez-Rodriguez MA., Molina-Holgado F., Molina-Holgado E. (2010). The Constitutive Production of the Endocannabinoid 2-Arachidonoylglycerol Participates in Oligodendrocyte Differentiation. Glia. 58:1913-1927.

Iuvone T., Esposito G., De Filippis D., Scuderi C., Steardo L. (2009). Cannabidiol: a promising drug for neurodegenerative disorders? CNS Neurosci Ther. 15(1):65-75.

Jarho, P., Pate DW., Brenneisen R., Jarvinen T. (1998). Hydroxypropyl-beta-cyclodextrin and its combination with hydroxypropyl-methylcellulose increases aqueous solubility of delta9-tetrahydrocannabinol. Life Sci. 63(26):PL381-384.

Jiang R, et al. (2011) Identification of cytochrome P450 enzymes responsible for metabolism of cannabidiol by human liver microsomes. Life Sciences. 89, 165-170.

Kren V, Rezanka T (2008) Sweet antibiotics—the role of glycosidic residues in antibiotic and antitumor activity and their randomization. FEMS Microbiol Rev. 32, 858-889.

Kren V (2008) Glycoside vs. Aglycon: The Role of Glycosidic Residue in Biologic Activity. Glycoscience. pp. 2589-2644.

Li S., Li W., Xiao Q., Xia Y. (2012). Transglycosylation of stevioside to improve the edulcorant quality by lower substitution using cornstarch hydrolyzate and CGTase. J Food Chem. 138(2013):2064-2069.

Mazur A., et al. (2009). Characterization of Human Hepatic and Extrahepatic UDP-Glucuronosyltransferase Enzymes Involved in the Metabolism of Classic Cannabinoids. Drug Metabolism and Disposition. 37(7): 1496-1504.

Mecha M., Torrao AS., Mestre L., Carrillo-Salinas FJ., Mechoulam R., Guaza C. (2012). Cannabidiol protects oligodendrocyte progenitor cells from inflammation-induced apoptosis by attenuating endoplasmic reticulum stress. Cell Death and Disease. 3(e331).

Mechoulam R., Parker LA., Gallily R. (2002). Cannabidiol: An Overview of Some Pharmacological Aspects. 42(S1):11S-19S.

Mighdoll MI., Tao R., Kleinman JE., Hyde TM. (2015). Myelin, myelin-related disorders, and psychosis. Schizophr Res. 161(1):85-93.

Molina-Holgado E., Vela JM., Arevalo-Martin A., Almazan G., Molina-Holgado F., Borrell J., Guaza C. (2002). Cannabinoids Promote Oligodendrocyte Progenitor Survival: Involvement of Cannabinoid Receptors and Phosphatidylinositol-3-Kinase/Akt Signaling. J. Neurosci. 22(22):9742-9753.

Noguchi A, et al. (2009). Identification of an inducible glucosyltransferase from Phytolacca americana L. cells that are capable of glucosylating capsaicin. Plant Biotechnology. 26, 285-292.

Pacher P, et al. (2006) The endocannabinoid system as an emerging target of pharmacotherapy. Pharmacology Review. 58(3), 389-462.

Richman A., Swanso, A., Humphrey T., Chapman R., McGarvey B., Pocs R., Brandle J. (2005). Functional genomics uncovers three (56) References Cited

OTHER PUBLICATIONS glucosyltransferases involved in the synthesis of the major sweet glucosides of Stevia rebaudiana. Plant J. 41(1):56-67.
Russo E., Guy, GW. (2006) A tale of two cannabinoids: the therapeutic rationale for combining tetrahydrocannabinol and cannabidiol. Medical Hypotheses. 66(2):234-46.
Terao J., Murota K., Kawai Y. (2011). Conjugated quercetin glucuronides as bioactive metabolites and precursors of aglycone in vivo. Food Function. 2:11-17.
Thomas A., et al. (2007) Cannabidiol displays unexpectedly high potency as an antagonist of CB1 and CB2 receptor agonists in vitro. British Journal of Pharmacology. 150, 613-623.
Watanabe K, et al. (1998) Distribution and characterization of anandamide amidohydrolase in mouse brain and liver. Life Sciences. 62(14), 1223-1229.
Yamaori S, et al. (2011) Potent inhibition of human cytochrome P450 3A isoforms by cannabidiol: Role of phenolic hydroxyl groups in the resorcinol moiety. Life Sciences, 88, 730-736.
Zuardi AW, et al. (2012). A Critical Review of the Antipsychotic Effects of Cannabidiol: 30 Years of a Translational Investigation. Current Pharmaceutical Design, 18, 5131-5140.
Bruni et al., Cannabinoid Delivery Systems for Pain and Inflammation Treatment, *Molecules*, 2018, 23, 2478, 25 pages.
Dewitte et al., "Screening of recombinant glycosyltransferases reveals the broad acceptor specificity of stevia UGT-76G1," *Journal of Biotechnology*, 233 (2016), pp. 49-55.
McPartland et al., "Affinity and Efficacy Studies of Tetrahydrocannabinolic Acid A at Cannabinoid Receptor Types One and Two," *Cannabis and Cannabinoid Research*, vol. 2.7, 2017,pp. 87-95.
Bowes, J. et al. "Reducing safety-related drug attrition: the use of in vitro pharmacological profiling." *Nature Reviews Drug Discovery*, 11, No. 12 (2012): 909.
Huestis, "Human Cannabinoid Pharmacokinetics," Chemistry & Biodiversity, vol. 4, (2007), pp. 1770-1804.
Friend, "New oral delivery systems for treatment of inflammatory bowel disease," *Advanced Drug Delivery Reviews*, 57 (2005), 247-265.
Friend et al., "Colon-specific drug delivery from a glucoside prodrug in the guinea-pig. Efficacy study," Journal of Controlled Release, vol. 15, No. 1, Feb. 1991, pp. 47-54.
Pertwee, Roger G. "Pharmacological actions of cannabinoids" in Cannabinoids, pp. 1-51. Springer, Berlin, Heidelberg, 2005.
Sartor, B. (2008) Microbial Influences in Inflammatory Bowel Diseases. Gastroenterology, 134, No. 2 (2008): 577-594.

\* cited by examiner

ANTIMICROBIAL COMPOSITIONS COMPRISING CANNABINOIDS AND METHODS OF USING THE SAME

CROSS-REFERENCE TO RELATED APPLICATIONS

The present application is a continuation of U.S. patent application Ser. No. 16/612,219, filed Nov. 8, 2019, which is a U.S. national phase application under 35 U.S.C. § 371 of International Application No. Application No. PCT/US2018/031727, filed May 9, 2018, which claims priority under 35 U.S.C. § 119(e) to U.S. Provisional Patent Application No. 62/503,417, filed May 9, 2017, the entire contents of which are incorporated herein by reference in their entireties for all purposes.

FIELD OF THE INVENTION

The invention relates to antimicrobial compositions comprising cannabinoid compounds and methods of utilizing the antimicrobial compositions to inhibit the growth of and/or kill microorganisms, to treat and/or prevent microbial infections.

BACKGROUND OF THE INVENTION

The World Health Organization (WHO) has declared that antibiotic resistance is one of the biggest threats to global health, food security, and development today. The United States Centers for Disease Control and Prevention (CDC) estimates that at a minimum there are 2,049,442 illnesses caused by antibiotic resistance resulting in 23,000 deaths annually.

Overuse of antibiotics is detrimental to the healthy intestinal microbiota, and can result in dysbiosis and microbial imbalances and overgrowths of pathogenic microbes such as *Clostridium difficile* (*C. difficile*). In 2015, the CDC estimated that nearly a half a million Americans suffered from *C. difficile* infections, which were directly responsible for 15,000 deaths and attributed to 29,000 total deaths (10).

The US Centers for Disease Control and Prevention (CDC) published a report in 2013 listing the top 18 drug-resistant threats to the United States. This list is divided into urgent, serious, and concerning threat levels. Included in the urgent threat list are *Clostridium difficile*, carbapenem-resistant Enterobacteriaceae, and cephalosporin-resistant *Neisseria gonorrhoeae*. Included in the serious threat list are multidrug-resistant *Acinetobacter*, drug-resistant *Campylobacter*, fluconazole-resistant *Candida*, extended spectrum beta-lactamase producing enterobacteriaceae, vancomycin-resistant *Enterococcus*, multidrug-resistant *Pseudomonas aeruginosa*, drug-resistant non-typhoidal *Salmonella*, drug-resistant *Salmonella typhi*, drug-resistant *Shigella*, methicillin-resistant *Staphylococcus aureus*, drug-resistant *Streptococcus pneumonia*, and drug-resistant tuberculosis. Included in the concerning threat list are vancomycin-resistant *Staphylococcus aureus*, erythromycin-resistant *Streptococcus* group A, and clindamycin-resistant *Streptococcus* group B (9).

In February 2017, the WHO published a list of priority pathogens for research and development of new antibiotics. This list is divided into three main groups of critical, high, and medium priority. Included in the critical list are carbapenem-resistant *Acinetobacter baumannii*, *Pseudomonas aeruginosa*, and Enterobacteriacea. Included in the high priority list are vancomycin-resistant *Enterococcus faecium*, methicillin-resistant and vancomycin intermediate and resistant *Staphylococcus aureus*, clarithromycin-resistant *Helicobacter pylori*, fluoroquinolone-resistant *Campylobacter* and *Salmonella* spp., and 3rd generation cephalosporin-resistant and fluoroquinolone-resistant *Neisseria gonorrhoeae*. Included in the medium priority list are penicillin-non-susceptible *Streptococcus pneumoniae*, ampicillin-resistant *Haemophilus influenzae*, and fluoroquinolone-resistant *Shigella* spp (15).

With the emergence of antimicrobial-resistance and the urgent threat to human health it represents, there is a critical need to develop novel antibiotics that are safe and effective. Van Klingern and Ten Ham observed that THC and CBD inhibited the growth of *Staphylococcus aureus* in the 1-5 µg/ml range (13). It has been shown that *Cannabis sativa indicus* extracts were effective as an antimicrobial agent towards *Clostridium perfringens* (12). Ali 2012 conducted antimicrobial testing of petroleum and alcohol extracts of *cannabis*. The extracts demonstrated activity against MRSA, but were ineffective against gram-negative bacteria and fungi (7). Appendino et al. 2008 published a structure-activity study comparing the structures of different cannabinoids for their ability to inhibit the growth of bacteria including MRSA (8).

To date, no evaluation of the antimicrobial activity of cannabinoids has been performed towards *Clostridium difficile* or *Enterococcus faecium*.

SUMMARY OF THE INVENTION

The present invention provides antimicrobial compositions comprising cannabinoids and methods of using the same. In certain aspects of the present invention, there is provided a composition having antimicrobial activity comprising a cannabinoid compound or a prodrug that is metabolized to the cannabinoid compound. In certain embodiments, the cannabinoid compound is cannabidiol, tetrahydrocannabinol, or a prodrug that is metabolized to cannabidiol or tetrahydrocannabinol, optionally a glycoside of cannabidiol or tetrahydrocannabinol. The composition may be formulated for oral administration or topical administration. In certain embodiments, the composition comprises a further active ingredient selected from other cannabinoid compounds, other antimicrobial agents, anti-inflammatory agents, probiotics and combinations thereof. The antimicrobial activity may be against gram positive aerobic bacteria and/or anaerobic bacteria.

In other aspects of the present invention, there is provided a method of treating an infection comprising applying to a patient in need thereof at the site of infection an effective amount of a topical composition comprising an effective amount of a cannabidiol or tetrahydrocannabinol in a pharmaceutically acceptable carrier for topical application. In certain embodiments, the infection is *S. pyogenes* infection.

In other aspects of the present invention, there is provided a method of treating microbial infections of the gastrointestinal tract, comprising oral administration of an effective amount of a cannabinoid compound. In certain embodiments, the cannabinoid compound is a glycoside of cannabidiol or tetrahydrocannabinol. In certain embodiments, the infection is a *C. difficile* infection; a methicillin-resistant *Staphylococcus aureus* infection or an *E. faecalis* infection.

In other aspects of the present invention, there is provided a method of inhibiting the growth of and/or killing microorganisms comprising administration of an effective amount of a cannabinoid compound. In certain embodiments, the microorganism is bacteria. In certain embodiments, the cannabinoid compound is cannabidiol or tetrahydrocannabinol.

DESCRIPTION OF THE FIGURES

These and other features of the invention will become more apparent in the following detailed description in which reference is made to the appended drawings.

DESCRIPTION OF THE INVENTION

The invention is based on the discovery that cannabinoid compounds inhibit the growth of and/or kill certain types of microorganisms. Accordingly, the present invention provides antimicrobial compositions comprising a cannabinoid compound alone or in combination with other agents and methods of utilizing the antimicrobial compositions to inhibit the growth of and/or kill microorganisms, to treat and/or prevent microbial infections.

The cannabinoid compounds include any cannabinoid compound which has antimicrobial activity or prodrugs thereof. A worker skilled in the art would readily appreciate that antimicrobial agents may have broad spectrum antimicrobial activity (i.e. activity against a wide range of microorganisms including bacteria, yeast, and fungus), may have antibacterial activity (i.e. activity against bacteria only), or may have activity against a selection of specific microorganisms or a single microorganism. For example, the agent may be active against gram-positive bacteria or gram-negative bacteria, may be active against aerobic bacteria or anaerobic bacteria or may be active against a subset thereof, for example, the agent may be active against gram-positive aerobes or gram-positive anaerobes. In certain embodiments, the cannabinoid compound has antimicrobial activity against gram-positive bacteria. In specific embodiments, the cannabinoid compound has antimicrobial activity against gram-positive aerobic bacteria. In other specific embodiments, the cannabinoid compound has antimicrobial activity against gram-positive anaerobic bacteria.

Non-limiting examples of gram-positive aerobic bacteria include *Staphylococcus aureus*, *Enterococcus faecalis*, *Streptococcus pneumonia* and *Streptococcus pyogenes*. In certain embodiments, the cannabinoid compound has antimicrobial activity against *Staphylococcus aureus*. In specific embodiments, the cannabinoid compound has antimicrobial activity against methicillin-sensitive *Staphylococcus aureus* (MSSA). In specific embodiments, the cannabinoid compound has antimicrobial activity against methicillin-resistant *Staphylococcus aureus* (MRSA). In certain embodiments, the cannabinoid compound has antimicrobial activity against *Enterococcus faecalis*. In specific embodiments, the cannabinoid compound has antimicrobial activity against vanomycin-sensitive *Enterococcus faecalis* (VSE). In specific embodiments, the cannabinoid compound has antimicrobial activity against vanomycin-resistant *Enterococcus faecalis* (VRE). In certain embodiments, the cannabinoid compound has antimicrobial activity against *Streptococcus pneumonia*. In certain embodiments, the cannabinoid compound has antimicrobial activity against *Streptococcus pygenes*.

Non-limiting examples of anaerobic bacteria include *Clostridium difficile, Lactobacillus crispatus, Lactobacillus jensenii, Bifidobacterium bifidum, Bifidobacterium longum* and *Bacteroides fragilis*. In certain embodiments, the cannabinoid compound has antimicrobial activity against *Clostridium difficile*. In certain embodiments, the cannabinoid compound has antimicrobial activity against *Lactobacillus* sp. In certain embodiments, the cannabinoid compound has antimicrobial activity against *Bifidobacterium* sp.

Antimicrobial activity may be microcidal (kills the microorganism) and/or biostatic (inhibits the growth of the microorganism). Accordingly, in certain embodiments, the cannabinoid compound exhibits microcidal activity. In certain embodiments, the cannabinoid compound inhibits the growth of microorganisms. In certain embodiments, the cannabinoid compound has microcidal activity. In certain embodiments, the cannabinoid compound has microcidal activity and also inhibits the growth of microorganisms.

The term "cannabinoid compound" as used herein generally refers to compounds found in *cannabis* or which act on cannabinoid receptors and also includes prodrugs thereof. The cannabinoid compounds may be isolated from *cannabis* or may be synthetic. cannabinoid compounds. The cannabinoid compounds include, but are not limited to, cannabidiol (CBD), cannabidivarin (CBDV), cannabigerol (CBG), tetrahydrocannabinol (Δ9-THC or THC), cannabinol (CBN), cannabidiolic acid (CBDA), tetrahydrocannabivarin (THCV), phytocannabinoids, endocannabinoids, and prodrugs thereof. In specific embodiments, the cannabinoid compound is cannabidiol. In specific embodiments, the cannabinoid compound is tetrahydrocannabinol.

The cannabinoid compounds may be in the form of a prodrug. A worker skilled in the art would readily appreciate that a prodrug is a compound which, upon administration, must undergo a chemical conversion by metabolic processes before becoming an active pharmacological agent (for example, have antimicrobial activity). Non-limiting examples of prodrugs include glycosides. In certain embodiments, the glycoside is a mono, di, tri or tetra-glycoside of the cannabinoid compound. The glucose residues of glycosides are commonly acid-hydrolyzed in the stomach or cleaved by glycosidase enzymes in the intestinal tract, including by alpha-glycosidases and beta-glycosidases, which are expressed by intestinal microflora across different regions of the intestine. Accordingly, glycosides are hydrolyzed upon ingestion to release the desired compound into the intestines or target tissues.

In certain embodiments, the cannabinoid compound is a cannabinoid glycoside prodrug which is capable of persisting in the acidic stomach environment upon oral administration and thereby allows for the delivery of the prodrug into the large intestine, where the cannabinoid aglycones can be liberated by glycosidases produced by colonic bacteria.

Figure 1A:
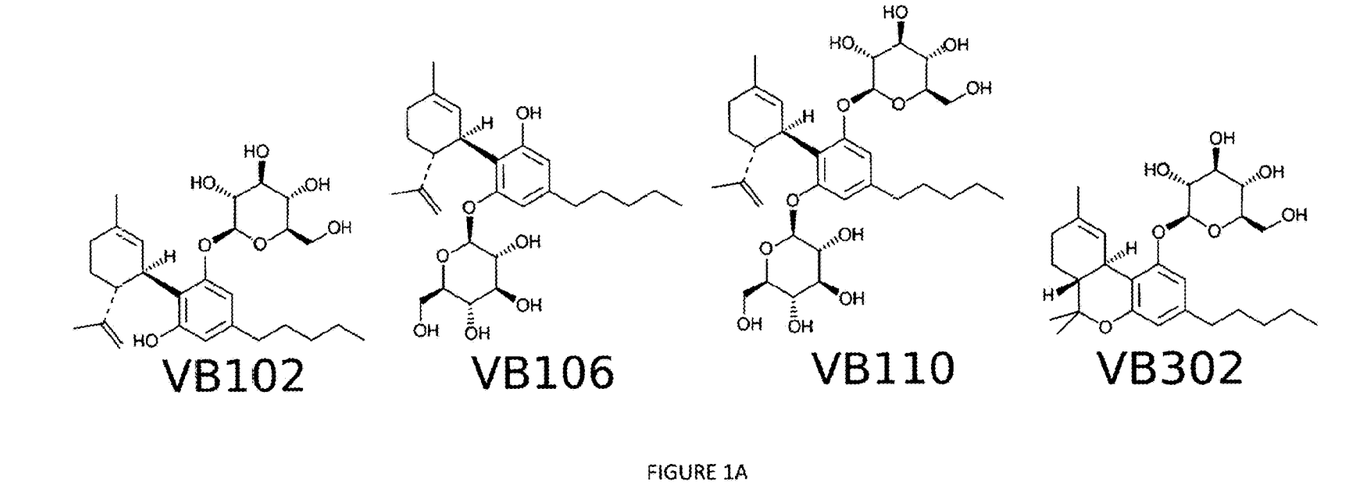
FIG. 1A provides the chemical structures of VB102, VB106, VB110 and VB302.
Figure 1B:
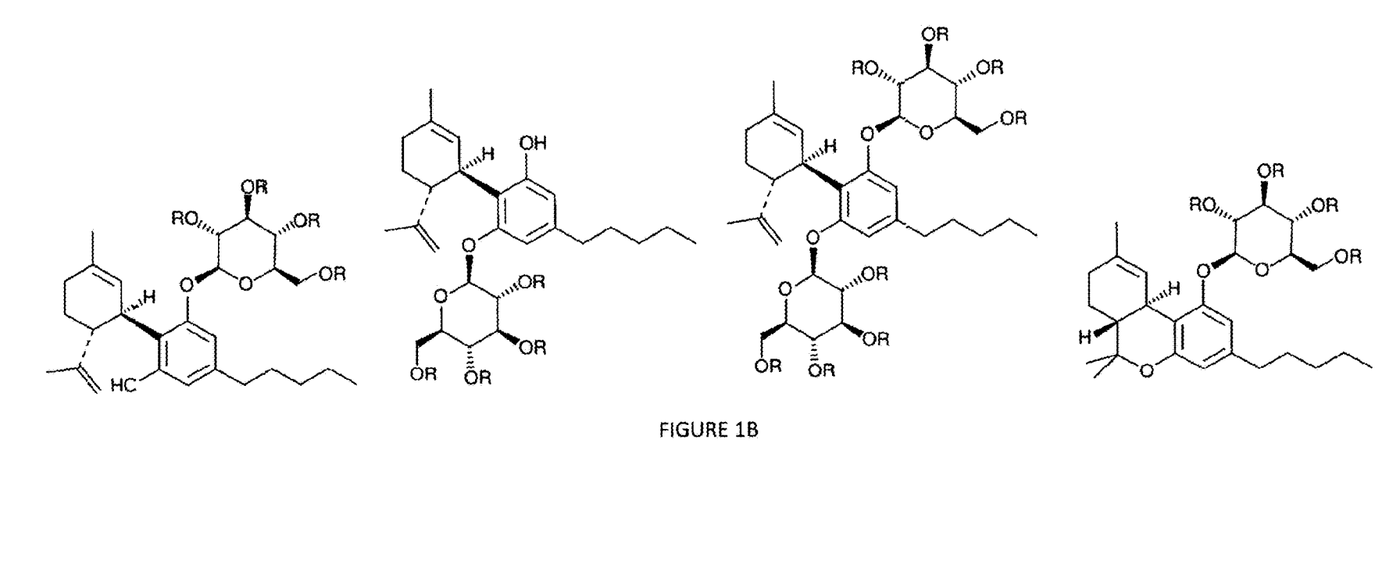
FIG. 1B provides the chemical structures of glycosides of cannabidiol and Δ9-THC; wherein each R is independently H, mono, di or tri-glycosidic residue.

In certain embodiments, the cannabinoid compound is a glycoside of cannabidiol. In specific embodiments, the glycoside of cannabidiol is a mono, di, tri or tetra-glycoside of cannabidiol. In specific embodiments, the glycoside of cannabidiol has a structure set forth in FIG. 1A, wherein each R is independently H, mono, di or tri-glycosidic residue. In specific embodiments, the glycoside of cannabidiol has a structure selected from VB102, VB106 and VB110 set forth in FIG. 1B.

In certain embodiments, the cannabinoid compound is a glycoside of tetrahydrocannabinol. In specific embodiments, the glycoside of tetrahydrocannabinol is a mono, di, tri or tetra-glycoside of tetrahydrocannabinol. In specific embodiments, the glycoside of tetrahydrocannabinol has a structure as set forth in FIG. 1A, wherein each R is independently H, mono, di or tri-glycosidic residue. In specific embodiments, the glycoside of tetrahydrocannabinol has the structure of VB302 as set forth in FIG. 1B.

The present invention also provides methods of utilizing the antimicrobial compositions. The antimicrobial compositions may be utilized to inhibit the growth of and/or kill microorganisms, and/or to treat and/or prevent microbial infections.

The antimicrobial compositions may be administered by various routes including but not limited to topical administration and oral administration. A person skilled in the art would readily appreciate that the cannabinoid compound used in the antimicrobial composition may be dependent on the administration route and microorganism. For example, such a person would readily appreciate that glycoside prodrugs are metabolized in the gastrointestinal tract for activity and as such may have optimal activity in oral drug formulations.

In certain embodiments, there is provided a method of treating a skin or wound infection comprising topically applying to a patient in need thereof at the site of infection an effective amount of a topical composition comprising an effective amount of a cannabinoid compound which has antimicrobial activity, including in a pharmaceutically acceptable carrier for topical application. In specific embodiments, the cannabinoid compound is cannabidiol. In specific embodiments, the cannabinoid compound is tetrahydrocannabinol. Appropriate pharmaceutically acceptable carriers are known in the art. In specific embodiments, the topical composition is for treatment of a wound is infected with methicillin-resistant *Staphylococcus aureus* or *Streptococcus pyogenes*.

In certain embodiments, there is provided a method of treating microbial infections of the gastrointestinal tract, comprising oral administration of an effective amount of a cannabinoid compound. The cannabinoid compound may be an active cannabinoid compound or a prodrug thereof. In specific embodiments, the cannabinoid compound is cannabidiol. In specific embodiments, the cannabinoid compound is a glycoside of cannabidiol. In specific embodiments, the glycoside of cannabidiol has a structure selected from structures set forth in FIGS. 1A and 1B. In specific embodiments, the cannabinoid compound is tetrahydrocannabinol or a glycoside of tetrahydrocannabinol. Optionally, the glycoside of tetrahydrocannabinol has a structure as set forth FIG. 1A or 1B.

In certain embodiments, the microbial infection of the gastrointestinal tract is a *Clostridium difficile* infection. In certain embodiments, the microbial infection of the gastrointestinal tract is a *Staphylococcus aureus* infection, including but not limited to methicillin-resistant *Staphylococcus aureus* (MRSA) infection. In certain embodiments, the microbial infection of the gastrointestinal tract is an *Enterococcus faecalis* infection, including but not limited to a vancomycin-resistant *Enterococcus faecalis* infection.

In certain embodiments, the compositions are used in methods of treating dysbiosis. In specific embodiments, the compositions are used in methods of treating dysbiosis of the gastrointestinal tract.

The cannabinoid compounds may have activities other than antimicrobial activities. For example, the compounds may have positive effects on the health of the skin or tissue epithelium, including the intestinal epithelium. For example, the compounds may exert anti-inflammatory effects.

In certain embodiments, the cannabinoid compound is inhibitory of harmful pathogens, and also has anti-inflammatory effects. In specific embodiments, the infection is a *C. difficile* infection and the compound is cannabidiol in the large intestine is inhibitory of harmful pathogens including *C. difficile*, and it also is anti-inflammatory, where it may help induce or maintain remission of colitis, which is often comorbid with *C. difficile* infections.

A person skilled in the art would appreciate that the compositions may include a single cannabinoid compound as the active ingredient or may further comprise other active ingredients including but not limited to other cannabinoid compounds, other antimicrobial agents, anti-inflammatory agents, and/or probiotics.

The following examples illustrate embodiments of the invention but should not be viewed as limiting the scope of the invention.

EXAMPLES

Example 1: Antimicrobial Activity of Cannabidiol and Prodrugs Thereof

Itemized Summary of Findings:
  CBD inhibits the growth of *Clostridium difficile* at 32 µg/ml (IC50)
  CBD inhibits the growth of methicillin-resistant *Staphylococcus aureus* (MRSA) at 2 µg/ml (IC50)
  CBD inhibits the growth of vancomycin resistant *Enterococcus faecalis* at 2 µg/ml (IC50)
  CBD inhibits the growth of *Streptococcus pneumoniae* at 4 µg/ml (IC50)
  CBD inhibits the growth of *Bacterioides fragilis* at 32 µg/ml (IC50)
  CBD inhibits the growth of healthy intestinal bacteria including *Lactobacillus crispatus, Lactobacillus jensenii, Bindobacterium bifidum, Bifidobacterium longum* (2 µg/ml, 64 ug/ml, 2 µg/ml, 32 µg/ml IC50 values respectively).
  CBD did not have any effect on the gram-negative pathogens *Klebsiella, Pseudomonas*, or *Acinetobacter*.

Introduction

The primary purpose of this study was to evaluate the in vitro susceptibility of a variety of clinically important microorganisms to cannabidiol (CBD), an active cannabinoid isolated from *cannabis*, and other cannabinoid prodrugs (VB104, VB110, and compounds listed in Table A). The in vitro activity of CBD and the cannabinoid prodrugs along with control agents (ciprofloxacin for aerobic bacteria, metronidazole for anaerobic bacteria, and amphotericin B for yeast/fungi) was determined by broth microdilution minimal inhibitory concentration (MIC) testing conducted in accordance with guidelines from the Clinical and Laboratory Standards Institute (CLSI; 1, 2).

Materials and Methods

Test Compounds

The cannabinoid prodrug test agents were stored at −20° C. prior to testing. Prodrugs were supplied as powders. CBD was supplied by Cayman Chemical as a 10 mg/mL methanolic solution and was stored at −20° C. after receipt. Prior to testing, using a 614 µL aliquot of the CBD methanolic solution, the methanol was dried off and the residual CBD was resuspended in 600 µL DMSO resulting in a 10.24 mg/mL solution. Stock solutions of comparator compounds were prepared on the day of testing using solvents recommended by CLSI. Stock solutions of all compounds were made at 40× the final testing concentration. Information regarding testing concentrations and drug diluent for the comparator and test agent is detailed in the table below.

| Test Agent | Testing Concentration Range (μg/ml) | Solvent/Diluent |
|---|---|---|
| Ciprofloxacin | 64-0.002 | Water/Water |
| Metronidazole | 32-0.03 | DMSO/Water |
| Amphotericin B | 64-0.06 | DMSO/DMSO |
| VB104 | 256-0.002 | DMSO/DMSO |
| VB304 | 256-0.002 | DMSO/DMSO |
| VB110 | 256-0.002 | DMSO/DMSO |
| CBD | 256-0.002 | DMSO/DMSO |

Test Organisms

The test organisms evaluated in this study consisted of clinical isolates from the Micromyx Repository and reference isolates from the American Type Culture Collection (ATCC; Manassas, VA). Upon initial receipt, the organisms were sub-cultured onto an appropriate agar medium. Following incubation, colonies were harvested from these plates and cell suspensions prepared and frozen at −80° C. with a cryoprotectant. Prior to testing, the isolates were streaked from frozen vials onto Trypticase Soy Agar with 5% sheep blood (BD; Sparks, MD; Lot No. 107682) for aerobic bacteria, Supplemented *Brucella* Agar (BD; Lot No. 6168880) for anaerobic bacteria, and Sabouraud Dextrose Agar (BD; Lot No. 6265646) for yeast. Aerobic bacteria were incubated at 35° C. overnight, anaerobic bacteria were incubated anaerobically at 35° C. for 48 hr, and yeast were incubated at 35° C. for 48 hr. *Aspergillus fumigatus* was previously streaked on SDA and incubated at 35° C. until spore formation occurred, followed by harvesting of the spores in sterile 0.85% saline and enumerating. Spore preparations were stored at 4° C.

Test Medium

Mueller Hinton II broth (MHB II; BD; Lot No. 6258541) was used for MIC testing of aerobic organisms. For *Streptococcus* isolates, this medium was supplemented with 3% laked horse blood (LHB; Cleveland Scientific, Bath, OH; Lot No. 343287). MIC testing of anaerobic bacteria was performed with *Brucella* broth (BD; Lot No. 1297468) supplemented with hemin (Sigma, St. Louis, MO; Lot No. SLBC4685V), vitamin K1 (Sigma; Lot No. MHBX5269V), and 5% LHB. Yeast and fungi were tested in RPMI-1640 from Hyclone Laboratories (Logan, UT; Lot No. AZC984041B) buffered with MOPs from Calbiochem (Billerica, MA; Lot No. 2730641).

Broth Microdilution MIC Methodology

MIC values were determined using a broth microdilution procedure described by CLSI (1-5). Automated liquid handlers (Multidrop 384, Labsystems, Helsinki, Finland; Biomek 2000 and Biomek FX, Beckman Coulter, Fullerton CA) were used to conduct serial dilutions and liquid transfers. To prepare the drug mother plates, which would provide the serial drug dilutions for the replicate daughter plates, the wells of columns 2-12 of standard 96-well microdilution plates (Costar 3795) were filled with 150 μl of the designated diluent for each row of drug. The test articles and comparator compounds (300 μl at 40× the highest concentration to be tested) were dispensed into the appropriate wells in column 1. The Biomek 2000 was then used to make 2-fold serial dilutions in the mother plates from column 1 through column 11. The wells of Column 12 contained no drug and served as the organism growth control wells for the assay. The daughter plates were loaded with 185 μL per well of the appropriate test medium for the tested organism using the Multidrop 384. The daughter plates were completed on the Biomek FX instrument which transferred 5 μL of drug solution from each well of a mother plate to the corresponding well of each daughter plate in a single step. Daughter plates for the testing of anaerobes were allowed to pre-reduce in the Bactron II anaerobe chamber for 2 hr prior to inoculation.

A standardized inoculum of each test organism was prepared per CLSI methods (1-5). The inoculum for each organism was dispensed into sterile reservoirs divided by length (Beckman Coulter), and the Biomek 2000 was used to inoculate the plates. Daughter plates were placed on the Biomek 2000 work surface reversed so that inoculation took place from low to high drug concentration. The plates were then inoculated with 10 μL of the inoculum resulting in a final concentration of approximately $5 \times 10^5$ CFU/mL (bacteria), 0.5 to $2.5 \times 10^3$ CFU/mL (yeast), and 0.2 to $2.5 \times 10^4$ CFU/mL (filamentous fungi) per well.

Plates were stacked 3-4 high, covered with a lid on the top plate, placed in plastic bags, and incubated at 35° C. for approximately 16 to 20 hr (aerobes), 20 to 24 hr (*Streptococcus*), and 24 and 48 hr (fungi). Anaerobe plates were stacked, covered with a lid on the top plate, placed in a BD GasPak EZ Anaerobe Container System and incubated at 35° C. for 48 hr. Following incubation, the microplates were removed from the incubator and viewed from the bottom using a plate viewer. For each of the test media and each drug, an un-inoculated solubility control plate was observed for evidence of drug precipitation. The MIC was read and recorded as the lowest concentration of drug that inhibited visible growth of the organism.

Results and Discussion

Compound precipitation observed with the uninoculated solubility controls is summarized in the following table.

| | Compound and lowest concentration (μg/mL) at which precipitation was observed | | | |
|---|---|---|---|---|
| Media type | VB104 | VB304 | VB110 | CBD |
| MHB II | TRP-16 | NA | none | TRP-16 |
| MHB II with Blood | TRP-128 | NA | NA | TRP-128 |
| *Brucella* Broth | NA | NA | NA | NA |
| RPMI | TRP-256 | NA | TRP-32 | NA |

NA = not applicable(no precipitation observed); TRP = trace precipitate; DCP = distinct precipitate Trace precipitation was noted for other compounds in various test medium, but in no instance did trace precipitation interfere with the reading of the MIC. The activity of CBD, the cannabinoid prodrugs, and control agents are shown in the tables below. Results for the control agents (ciprofloxacin, metronidazole, and amphotericin B) were all within the established CLSI QC ranges (2, 6) for the respective agents and quality control organisms.

A pro-drug must typically undergo a chemical conversion by metabolic processes before becoming an active pharmacological agent. Accordingly, the cannabinoid prodrugs (prior to chemical conversion to cannabidiol) were inactive towards gram-positive and -negative aerobic bacteria, CBD was active against gram-positive aerobes but was inactive against gram-negative aerobes. Ciprofloxacin activity was as expected for a broad spectrum anti-bacterial agent, with resistance apparent for the evaluated MRSA, VRE, and KPC-2 isolates where fluoroquinolone-resistance is commonly encountered.

Activity of Cannabinoid Prodrugs, Cannabidiol (CBD), and Ciprofloxacin Against Aerobic Bacteria

| | Organism | Isolate No. | MIC (μg/mL) | | | | |
|---|---|---|---|---|---|---|---|
| | | | VB104 | VB304 | VB110 | CBD | Ciprofloxacin |
| Gram-positive | Staphylococcus aureus (MSSA) | MMX 100 (ATCC 29213) | >256 | >256 | >256 | 2 | 0.5 (0.12-0.5)[1] |
| | Staphylococcus aureus (MRSA) | MMX 757 | >256 | >256 | >256 | 2 | >64 |
| | Enterococcus faecalis (VSE) | MMX 101 (ATCC 29212) | >256 | >256 | >256 | 2 | 1 (0.25-2)[1] |
| | Enterococcus faecalis (VRE) | MMX 848 | >256 | >256 | >256 | 2 | 32 |
| | Streptococcus pneumoniae | MMX 1195 (ATCC 49619) | >256 | >256 | >256 | 4 | 1 |
| | Streptococcus pyogenes | MMX 404 | >256 | >256 | >256 | 16 | 0.5 |
| Gram-negative | Escherichia coli | MMX 102 (ATCC 25922) | >256 | >256 | >256 | >256 | 0.008 (0.004-0.015)[1] |
| | Klebsiella pneumoniae (KPC-2) | MMX 4683 | >256 | >256 | >256 | >256 | >64 |
| | Pseudomonas aeruginosa | MMX 1380 | >256 | >256 | >256 | >256 | 4 |
| | Acinetobacter baumannii | MMX 1630 | >256 | >256 | >256 | >256 | 1 |

MSSA = methicillin-susceptible *S. aureus*;
MRSA = methicillin-resistant *S. aureus*;
VSE = vancomycin-susceptible enterococci;
VRE = vancomycin-resistant enterococci;
KPC-2 = *Klebsiella pneumoniae* carbapenemase-positive
[1] CLSI QC range shown in parenthesis As shown in the table below, CBD was active with MICs from 2-64 μg/mL. Metronidazole was active against all organisms with the exception of the evaluated *Lactobacillus* spp., which is consistent with the anticipated activity for these isolates.

Activity of Cannabinoid Prodrugs, Cannabidiol (CBD), and Metronidazole Against Anaerobic Bacteria

| Organism | Isolate No. | MIC (μg/mL) | | | | |
|---|---|---|---|---|---|---|
| | | VB104 | VB304 | VB110 | CBD | Metronidazole |
| *Clostridium difficile* | MMX 4381 (ATCC 00057) | >256 | >256 | >256 | 32 | 0.12 |
| *Clostridium difficile* | MMX 8330 | >256 | >256 | >256 | 32 | 0.12 |
| *Clostridium difficile* | MMX 8333 | >256 | >256 | >256 | 32 | 0.5 |
| *Lactobacillus crispatus* | MMX 4147 | >256 | >256 | >256 | 2 | >32 |
| *Lactobacillus jensenii* | MMX 4149 | >256 | >256 | >256 | 64 | >32 |
| *Bifidobacterium bifidum* | MMX 3965 | >256 | >256 | >256 | 2 | 1 |
| *Bifidobacterium longum* | MMX 3968 | >256 | >256 | >256 | 32 | 8 |
| *Bacteroides fragilis* | MMX 123 (ATCC 5285) | >256 | >256 | >256 | 32 | 0.5 (0.25-2)[1] |

[1] CLSI QC range shown in parenthesis

Neither the cannabinoid prodrugs or CBD were active against the evaluated yeast and fungal isolates though it is important to note that some inhibition of growth (50% relative to the growth control) was apparent with VB304 at 24 hr against *C. parapsilosis* at the highest test concentration (256 μg/mL) and for VB110 at 24 and 48 hr against *C. parapsilosis* at concentrations >16 μg/mL. Amphotericin B had the expected activity against both test isolates.

Activity of Cannabinoid Prodrugs, Cannabidiol (CBD), and Amphotericin B Against Yeast and Fungi

| Organism | Isolate No. | MIC (µg/mL) at 24, 48 hr | | | | Amphotericin B |
|---|---|---|---|---|---|---|
| | | VB104 | VB304 | VB110 | CBD | |
| Candida parapsilosis | MMX 2323 (ATCC 22019) | >256, >256 | >256[1], >256 | >256[2], >256[2] | >256, >256 | 0.5 (0.5-2)[3] 1 (0.25-4)[3] |
| Aspergillus fumigatus | MMX 5280 (ATCC MYA-3626) | >256, >256 | >256, >256 | >256, >256 | >256, >256 | 0.5, 2 (0.5-4)[3] |

[1] 50% inhibition observed at 256 µg/mL relative to the growth control
[2] 50% inhibition observed at ≥16 µg/mL relative to the growth control
[3] CLSI QC ranges shown in parenthesis In summary, CBD was active against gram-positive aerobic bacteria (*S. aureus, E. faecalis, S. pneumoniae*, and *S. pyogenes*) and both obligate and facultative anaerobes (*C. difficile, B. fragilis, Bifidobacterium* spp., and *Lactobacillus* spp.), but not gram-negative aerobic bacteria or yeast and fungi. The cannabinoid prodrugs had no in vitro activity against any of the evaluated microorganisms, though some inhibitory activity against the tested yeast isolate was noted for VB110.

As shown in the following examples, the cannabinoid prodrugs are metabolized in the large intestine to release active compound. Accordingly, a person skilled in the art would expect these prodrugs to have antimicrobial activity following oral administration.

Example 2: Bioavailability Assay

Figure 2A:
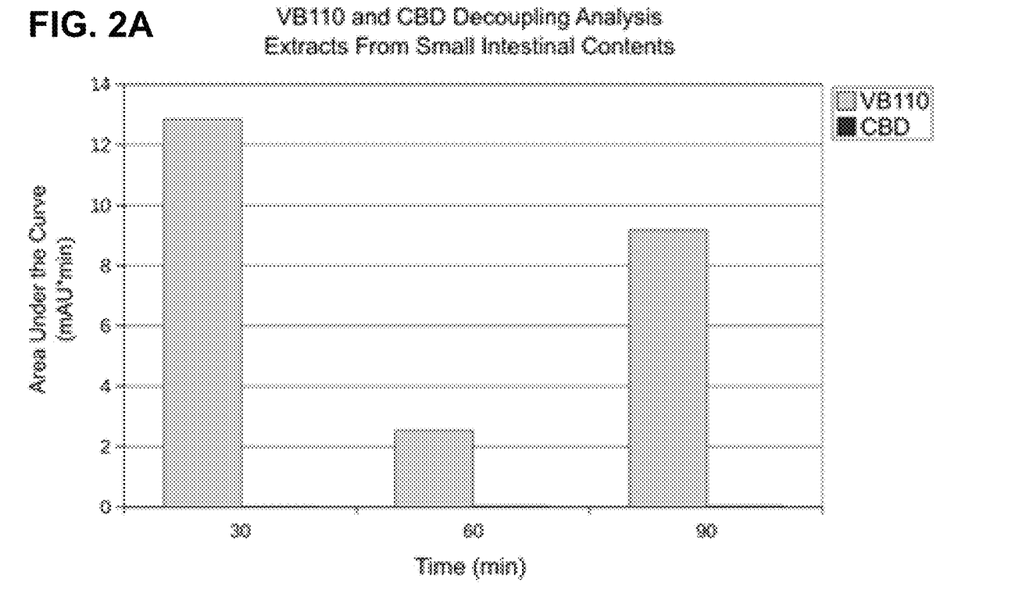
FIG. 2A illustrates VB110 and CBD decoupling analysis of extracts from small intestinal contents.
Figure 2B:
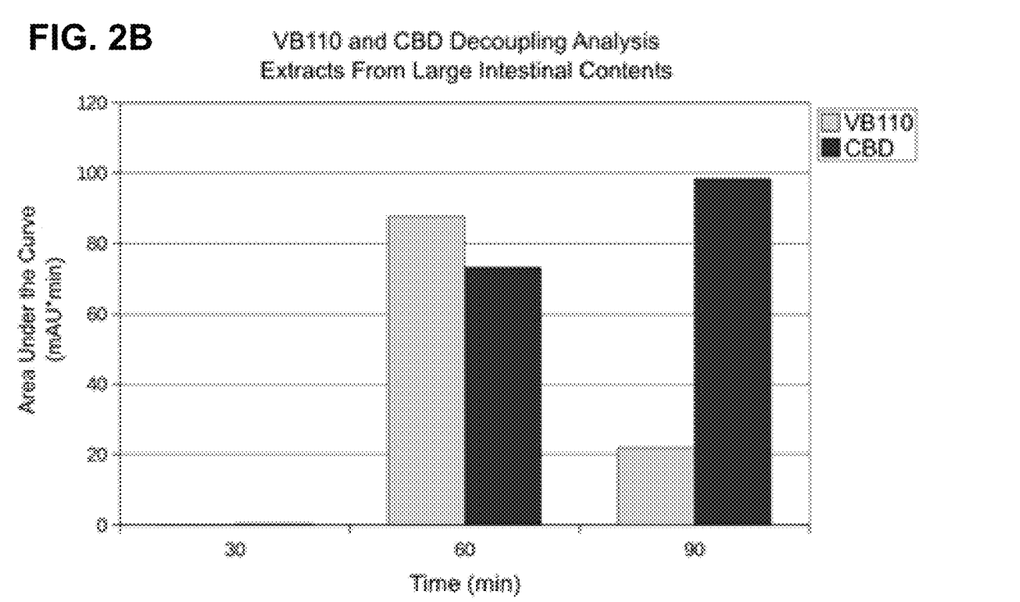
FIG. 2B illustrates VB110 and CBD decoupling analysis of extracts from large intestinal contents.

In order to investigate the effectiveness of glycosylation to effect site-specific drug delivery, VB110 was administered to three mice by oral gavage and the animals sacrificed at 30, 60, and 90 minutes. Eight-week old male Swiss mice were fasted for 12 hours prior to administration of 120 mg/kg VB110 in 10% Ethanol USP, 10% Propylene Glycol USP, 0.05% Sodium Deoxycholate USP, 79.95% Saline USP. Following termination and tissue harvest, the intestinal contents were then extracted and analyzed by C18 reverse phase HPLC. As shown in FIG. 2A, the small intestinal contents showed intact VB110, but no decoupled CBD. As shown in FIG. 2B, the large intestinal contents contained both VB110 and CBD in the 60 and 90 minute time points. This decoupling of VB110 is consistent with the large intestinal decoupling seen for sennoside beta-glycosides and is the result of secreted beta-glycosidases from the large intestinal microflora.

Example 3: Analysis of Large Intestine Contents Upon Administration of CBD and CBD Glycosides In order to investigate the metabolism and decoupling of CBD-glycosides in the large intestine, an aqueous solution of a mixture of CBD-glycosides was administered to a mouse by oral gavage. As a control, a solution of CBD in cremophor, ethanol, and saline was administered to a second mouse. The animals were each sacrificed at 2 hours. Following termination and tissue harvest, the intestinal contents were then extracted and analyzed by C18 reverse phase HPLC. The mice employed in this example were eight week old male Swiss mice fasted for 12 hours prior to administration of the solutions.

The resulting extracts were analyzed by LCMS performed using a Shimadzu LC-MS 2010 E V. Electrospray ionization (ESI) was performed in negative mode. The column was a Silia Chrom XDB C18 5 um, 150A, 4.6×50 mm. The method was 12 min 5 to 95 $H_2O$:ACN. Acetic acid and formic acid were used as sample additives during analysis, and the injection volume was 20 µl.

Analysis of the large intestinal contents of animals administered a mixture of oral CBD-glycosides indicated that both aglycone and glycosides were present, along with hydroxy metabolites of each:

[CBD–H], [2CBD–H] and [CBD*2OH+Formic acid–H] MS data: LC/ESI-LRMS. $[M-H]^-$ $(C_{21}H_{29}O_2)$ Calcd: m/z=313. Found: m/z=313. $[2M-H]^-$ $(C_{42}H_{59}O_4)$ Calcd: m/z=627. Found: m/z=627. $[M_{+2OH}+$Formic acid–H] $(C_{22}H_{31}O_6)$ Calcd: m/z=391. Found: m/z=391. [CBDg1–H], [CBDg1+Cl] and [2CBDg1–H] MS data: LC/ESI-LRMS. $[M_{g1}-H]^-$ $(C_{27}H_{39}O_7)$ Calcd: m/z=475. Found: m/z=475. $[M_{g1}+Cl]^-$ $(C_{27}H_{40}O_7Cl)$ Calcd: m/z=511. Found: m/z=511. $[2M_{q1}-H]^-$ $(C_{54}H_{79}O_{14})$ Calcd: m/z=951. Found: m/z=951.

[CBDg2–H] and [CBDg2+Acetic acid–H] MS data: LC/ESI-LRMS. $[M_{g2}-H]^-$ $(C_{33}H_{49}O_{12})$ Calcd: m/z=637. Found: m/z=637. $[M_{g2}+$Acetic acid–H$]^-$ $(C_{35}H_{53}O_{14}^-)$ Calcd: m/z=697. Found: m/z=697.

[CBDg3–H], [CBDg3*OH–H] and [CBDg3*OH–2H] MS data: LC/ESI-LRMS. $[M_{g3}-H]^-$ $(C_{39}H_{59}O_{17})$ Calcd: m/z=799. Found: m/z=799. $[M_{g3*OH}-H]^-$ $(C_{39}H_{59}O_{18})$ Calcd: m/z=815. Found: m/z=815. $[M_{g3*OH}-2H]^{-2}$ $(C_{39}H_{58}O_{18})$ Calcd: m/z=407. Found: m/z=407.

Analysis of the Large Intestinal Contents of Animals Administered Oral CBD Indicated that Hydroxy

[CBD*2OH+Formic acid–H] and [2CBD*3OH+Acetic acid–H] MS data: LC/ESI-LRMS. $[M_{+2OH}+$Formic acid–H$]^-$ $(C_{22}H_{31}O_6^-)$ Calcd: m/z=391. Found: m/z=391. $[2M_{*3OH}+$Acetic acid–H$]^-$ $(C_{44}H_{63}O_{12}^-)$ Calcd: m/z=783.9. Found: m/z=784.

The plasma and brains from the same animals were also extracted and analyzed by HPLC for the presence of CBD-glycosides and CBD. CBD was only present in the control animal that received CBD aglycone (data not shown). The contents of the small intestines from the same animals were also extracted and analyzed by HPLC for the presence of CBD-glycosides and CBD, but no CBD aglycone was present in the small intestines (data not shown). The presence of the CBD aglycone in the large intestinal contents indicates the successful delivery of CBD-glycosides, and the subsequent hydrolysis of the glycosides by beta-glycosidase enzymes only present in the large intestine. The presence of decoupled CBD in the large intestine, but not in the small intestine, indicates that glycoside decoupling only occurs upon transit to the large intestine. The presence of CBD detoxification metabolite CBD-2OH is also consistent with delivery of CBD and absorption into the intestinal epithelium where CBD begins to be metabolized. This example illustrates the potential to administer CBD-glycosides, safely transit the CBD-glycosides through the small intestine without absorption, transit to the large intestine where the sugars can be decoupled to release CBD locally, avoiding systemic absorption and delivery of the CBD to other tissues where it can have unwanted effects.

Example 4: In Vitro Activity of Cannabidiol and Tetrahydrocannabinol Against a Diverse Array of Microbes Including Aerobic and Anaerobic Bacteria, Yeast, and Fungi Introduction The antimicrobial activity of tetrahydrocannabinol (THC) and cannabidiol (CBD) was evaluated. The following example describes determining the Minimal Inhibitory Concentration (μg/mL) of these two compounds using industry-accepted protocols published by the Clinical Laboratory Standards Institute (CLSI; 1-6). In order to evaluate the spectrum of antimicrobial activity, these compounds were tested against aerobic bacteria, anaerobic bacteria, yeast, and fungi. Each compound was tested alone and in combination as described below.

Methods

Test Compounds and Comparators

The tetrahydrocannabinol (THC) and cannabidiol (CBD) were stored at −20° C. prior to testing. The compounds were supplied in methanol at 10 mg/mL (CBD) or 1 mg/mL (THC). Stock solutions of each compound were prepared by drying the methanol suspension and resuspending in DMSO to provide an 80× stock. The comparator drugs ciprofloxacin, metronidazole, and amphotericin B were provided by Micromyx. Stock solutions of the comparators were prepared at 40× on the day of testing and allowed to stand for at least 1 hr prior to use to auto-sterilize. Solvent, and working stock concentrations were as follows:

| Test/Control Agents | Solvent/ Diluent | Testing Range (μg/mL) |
| --- | --- | --- |
| THC—delta 9-THC | DMSO | 128-0.002 |
| CBD—Cannabidiol | DMSO | 128-0.002 |
| Ciprofloxacin | Water | 64-0.002 |
| Metronidazole | DMSO | 32-0.03 |
| Amphotericin B | DMSO | 64-0.06 |

Test Organisms

The test organisms for the assay were clinical isolates from the Micromyx repository or reference strains acquired from the American Type Culture Collection (ATCC, Manassas, VA). Upon receipt, the isolates were streaked onto the appropriate agar plates and incubated at optimal conditions for growth. Colonies were harvested from these plates and a cell suspension was prepared in the appropriate media containing cryoprotectant. Aliquots were then frozen at −80° C. Prior to the assay, the isolates were streaked for isolation from frozen stocks onto the appropriate agar plates and incubated at optimal conditions for growth.

Test Media

The media employed for testing the isolates was Mueller Hinton Broth (MHB II; BD; Lot No. 5257869) for aerobic organisms. For streptococci, this medium was supplemented with 3% laked horse blood (LHB; Cleveland Scientific, Bath, OH; Lot No. 369595). MIC testing of anaerobic bacteria was performed with *Brucella* broth (BD; Lot No. 6155858) supplemented with hemin (Sigma, St. Louis, MO; Lot No. SLB46854), vitamin K1 (Sigma; Lot No. MKBN5958V) and 5% LHB. Yeast and fungi were tested in RPMI 1640 (Hyclone Laboratories, Logan, UT; Lot No. AZC184041A) buffered with MOPS from Calbiochem (Billerica, MA; Lot No. 2875157).

All the above media was prepared/stored according to guidelines from the Clinical and Laboratory Standards Institute (CLSI; 1-5).

Broth Microdilution MIC Testing

MIC values were determined using the broth microdilution method as recommended by CLSI (1-5). Automated liquid handlers (Multidrop 384, Labsystems, Helsinki, Finland; Biomek 2000 and Biomek FX, Beckman Coulter, Fullerton CA) were used to conduct serial dilutions and liquid transfers.

To prepare the drug mother plates, which would provide the serial drug dilutions for the replicate daughter plates, the wells of a standard 96-well microdilution plate (Costar 3795, Corning Inc., Corning, NY) were filled with 150 μL of the designated diluent in columns 2-12. The wells of column 1 were filled with either 300 μL of 40× of the appropriate compound or 150 μL of either 40× or 80× of the test articles to make final concentrations of the combinations as shown below. A 150 μL volume of solution was transferred from the wells in Column 1 to make ten subsequent 2-fold serial dilutions from columns 2-11. The wells of Column 12 contained no drug and ultimately served as the organism growth control wells. For the test articles, this resulted in the following dilutions and concentrations in each row of the respective mother plates:

| Mother Plate 1 | | | | | | | | |
| --- | --- | --- | --- | --- | --- | --- | --- | --- |
| Row No. → | A | B | C | D | E | F | G | H |
| Dilution → | 128-0.12 | 2-0.002 | 128/64-0.12/0.06 | 2/1-0.002/0.001 | 128/128-0.12/0.12 | 2/2-0.002/0.002 | 64/128-0.06/0.12 | 1/2-0.001/0.002 |
| THC → | 40× | 40× | 80× | 80× | 80× | 80× | 40× | 40× |
| CBD → | None | None | 40× | 40× | 80× | 80× | 80× | 80× |
| Ratio THC:CBD | 1:0 | 1:0 | 2:1 | 2:1 | 1:1 | 1:1 | 1:2 | 1:2 |

| Mother Plate 2 | |
| --- | --- |
| Row No. → | |
| A | B |
| Dilution → 128-0.12 | 2-0.002 |
| THC → None | None |
| CBD → 40× | 40× |
| Ratio THC:CBD 0:1 | 0:1 |

The daughter plates were loaded with 185 µL per well of the appropriate test medium for the tested organism. They were then completed with a transfer of 5 µL of drug solution from each well of the mother plate to the corresponding well of each daughter plate in a single step. Daughter plates used for testing of anaerobes were allowed to pre-reduce in anaerobe boxes for at least 2 hr prior to inoculation.

A standardized inoculum of each organism was prepared per CLSI methods (1-5). Suspensions were prepared in sterile saline to equal the turbidity of a 0.5 McFarland standard, diluted in appropriate media per CLSI recommendations, and transferred to compartments of sterile reservoirs divided by width (Beckman Coulter). The Biomek 2000 (Beckman Coulter, Fullerton CA) was used to inoculate all. Daughter plates for the organisms were placed on the Biomek 2000 in reverse orientation. The Biomek 2000 delivered 10 µL of standardized inoculum into each well of the appropriate plate resulting in a final concentration of approximately $5\times10^5$ CFU/mL (bacteria), 0.5 to $2.5\times10^3$ CFU/mL (yeast), and 0.2 to $2.5\times10^4$ CFU/mL (filamentous fungi) per well.

Plates were stacked 3-4 high, covered with a lid on the top plate and incubated according to CLSI methodology. Aerobes were incubated for approximately 16-20 hr, *Streptococcus* for 20-24 hr, and anaerobes, yeast, and fungi for 24-48 hr. After incubation, plates were viewed from the bottom using a plate viewer.

Un-inoculated solubility control plates for each test media and drug were incubated in parallel with test plates and observed for evidence of drug precipitation. MICs were read where visible growth of the organism was inhibited.

Results and Discussion

Compound precipitation observed with the uninoculated solubility controls is summarized in the table below.
Compound Precipitation Observed with the Uninoculated Solubility Controls Distinct or trace precipitation at the highest test concentration (128 µg/mL) was observed for THC, THC/CBD 1:1, and THC/CBD 1:2 in MHB II without blood, RPMI, and *Brucella* broth. However, the nature of the precipitate permitted reading growth of the organisms through 128 µg/mL.

The activity of CBD, THC, and the control agents are shown in the tables below. Results for the control agents (ciprofloxacin, metronidazole, and amphotericin B) were all within the established CLSI QC ranges (2, 6) for the respective agents and quality control organisms.

Against Gram-positive and -negative aerobic bacteria, CBD and THC tested alone were active against Gram-positive aerobes with MIC values of 1-4 µg/mL, but were inactive against Gram-negative aerobes. The MIC values for CBD were similar to those observed in a previous study. Ciprofloxacin activity was as expected for a broad spectrum anti-bacterial agent, with resistance apparent for the evaluated MRSA, VRE, and KPC-2 isolates where fluoroquinolone-resistance is commonly encountered.

As shown in the table below, THC and CBD displayed similar activity against the evaluated anaerobes, with MICs from 16→128 µg/mL (THC) and 8→128 µg/mL (CBD). MIC values for CBD were within 2-fold of a previous study, with the exceptions of *B. bifidum* where the previous MIC was 2 µg/mL and *B. fragilis* where the previous MIC was 32 µg/mL. Metronidazole was active against all organisms with the exception of the evaluated *Lactobacillus* spp. which is consistent with the anticipated activity for these isolates.

Combinations of THC and CBD did not display enhanced anti-microbial activity against evaluated microbes. This suggests that CBD and THC are functional analogs, and the antimicrobial activity is based on their hydrophobicity and affinity for the cell membranes.

Neither THC nor CBD were active against the evaluated yeast and fungal isolates. Amphotericin B had the expected activity against both test isolates.

In summary, CBD and THC were active against Gram-positive aerobic bacteria (*S. aureus, E. faecalis, S. pneumoniae*, and *S. pyogenes*) and both obligate and facultative anaerobes (*C. difficile, Bifidobacterium* spp., and *Lactobacillus* spp.), but not Gram-negative aerobic bacteria, yeast, and fungi.

| | Compound and lowest concentration (µg/mL) at which precipitation was observed | | | | |
|---|---|---|---|---|---|
| Media type | THC | CBD | THC/CBD 2:1 | THC/CBD 1:1 | THC/CBD 1:2 |
| MHB II | DCP 64, 128 | none | none | DCP 128/128 64/64 | DCP 64/128 32/64 |
| MHB II with Blood | none | none | none | none | none |
| *Brucella* Broth | DCP 128 | none | none | none | none |
| RPMI | TRP 128, 64, 32, 16 | none | none | TRP 128/128, 64/64, 32/32, 16/16 | TRP 64/128, 32/64, 16/32 |

None = (no precipitation observed); TRP = trace precipitate; DCP = distinct precipitate Activity of THC, CBD, and THC:CBD Combinations Against Aerobic Bacteria.

|  | Organism | Isolate No. | MIC (µg/mL) | | | | | |
|---|---|---|---|---|---|---|---|---|
|  |  |  | THC | CBD | THC/CBD 2:1 | THC/CBD 1:1 | THC/CBD 1:2 | Ciprofloxacin |
| Gram-positive | Staphylococcus aureus (MSSA) | MMX 100 (ATCC 29213) | 2 | 2 | 4/2 | 2/2 | 1/2 | 0.25 (0.12-0.5)[1] |
|  | Staphylococcus aureus (MRSA) | MMX 757 | 2 | 2 | 4/2 | 2/2 | 1/2 | >64 |
|  | Enterococcus faecalis (VSE) | MMX 101 (ATCC 29212) | 2 | 2 | 4/2 | 2/2 | 1/2 | 1 (0.25-2)[1] |
|  | Enterococcus faecalis (VRE) | MMX 848 | 2 | 2 | 4/2 | 2/2 | 1/2 | 64 |
|  | Streptococcus pneumoniae | MMX 1195 (ATCC 49619) | 1 | 4 | 8/4 | 1/1 | 1/2 | 0.5 |
|  | Streptococcus pyogenes | MMX 404 | 16 | 32 | 64/32 | 64/64 | 32/64 | 0.25 |
| Gram-negative | Escherichia coli | MMX 102 (ATCC 25922) | >128 | >128 | >128/64 | >128/128 | >64/128 | 0.008 (0.004-0.015)[1] |
|  | Klebsiella pneumoniae (KPC-2) | MMX 4683 | >128 | >128 | >128/64 | >128/128 | >64/128 | >64 |
|  | Pseudomonas aeruginosa | MMX 1380 | >128 | >128 | >128/64 | >128/128 | >64/128 | 4 |
|  | Acinetobacter baumannii | MMX 1630 | >128 | >128 | >128/64 | >128/128 | >64/128 | 4 |

MSSA = methicillin-susceptible *S. aureus*;
MRSA = methicillin-resistant *S. aureus*;
VSE = vancomycin-susceptible enterococci;
VRE = vancomycin-resistant enterococci;
KPC-2 = *Klebsiella pneumoniae* carbapenemase-positive
[1]CLSI QC range shown in parenthesis Activity of THC, CBD, and THC:CBD Combinations Against Anaerobic Bacteria

| Organism | Isolate No. | MIC (µg/mL) | | | | | |
|---|---|---|---|---|---|---|---|
|  |  | THC | CBD | THC/CBD 2:1 | THC/CBD 1:1 | THC/CBD 1:2 | Metronidazole |
| Clostridium difficile | MMX 4381 (ATCC 700057) | 32 | 64 | >128/64 | 64/64 | 32/64 | 0.25 |
| Clostridium difficile | MMX 8330 | 32 | 64 | >128/64 | 32/32 | 32/64 | 0.25 |
| Clostridium difficile | MMX 8333 | 32 | 64 | 64/32 | 32/32 | 16/32 | 2 |
| Lactobacillus crispatus | MMX 4147 | No growth | No growth | No growth | No growth | No growth | No growth |
| Lactobacillus jensenii | MMX 4149 | 128 | >128 | >128/64 | >128/128 | >64/128 | >32 |
| Bifidobacterium bifidum | MMX 3965 | 16 | 8 | 8/4 | 4/4 | 8/16 | 2 |
| Bifidobacterium longum | MMX 3968 | 32 | 64 | >128/64 | 64/64 | 32/64 | 8 |
| Bacteroides fragilis | MMX 123 (ATCC 25285) | >128 | >128 | >128/64 | >128/128 | >64/128 | 0.5 (0.25-2)[1] |

[1]CLSI QC range shown in parenthesis

Activity of THC, CBD, and THC:CBD Combinations Against Fungi.

| | | MIC (μg/mL) at 24, 48 hr | | | | | |
|---|---|---|---|---|---|---|---|
| Organism | Isolate No. | THC | CBD | THC/CBD 2:1 | THC/CBD 1:1 | THC/CBD 1:2 | Amphotericin B |
| Candida parapsilosis | MMX 2323 (ATCC 22019) | >128 (4[1]), >128 (4[1]) | >128, >128 | >128/64 (16/8[1]), >128/64 (16/8[1]) | >128/128 (32/32[1]), >128/128 (32/32[1]) | >64/128 (16/32[1]), >64/128 (16/32[1]) | 0.12 (0.5-2)[3], 0.5 (0.25-4)[3] |
| Aspergillus fumigatus | MMX 5280 (MYA-3626) | >128, >128 | >128, >128 | >128/64, <128/64 | >128/128, >128/128 | >64/128, >64/128 | 0.25, 1 (0.5-4)[3] |

[1]50% inhibition observed at XXX μg/mL relative to the growth control
[2]50% inhibition observed at XXX μg/mL relative to the growth control
[3]CLSI QC ranges shown in parenthesis Example 5: Determination of Minimal Inhibitory Concentration (μg/mL) and Minimum Bactericidal Concentration (MBC) of Cannabidiol and Tetrahydrocannabinol for a Variety of Aerobic and Anaerobic Bacteria The test agents (THC and CBD) were be dried and resuspended in 100% DMSO as described above. MIC/MBC testing utilized a drug concentration range of 128-0.12 μg/mL. For aerobic organisms only, imipenem was tested using a concentration range of 8-0.008 μg/mL to serve as a quality control drug for MIC testing (MBC testing for imipenem was conducted for *E. coli* ATCC 25922 as a quality control MBC test). For anaerobic testing, metronidazole was tested as the quality control antibiotic for MIC testing using a concentration range of 32-0.03 μg/mL (no MBC testing). In all 96-well plates, the twelfth well of each row did not contain drug and will serve as the positive growth control.

The broth microdilution MIC methodology followed the procedures described by the Clinical Laboratory Standards Institute (CLSI) and employed automated liquid handlers to conduct serial dilutions and liquid transfers. Following incubation, the microplates were removed from the incubator and viewed from the bottom using a Scienceware plate reader. The solubility control plate was observed for evidence of drug precipitation. The MIC was read and recorded as the lowest concentration of drug that inhibited visible growth of the organism.

The MBC was evaluated for THC and CBD only, in parallel with the MIC in accordance with CLSI guidelines. After determining the MIC, concentrations or wells at the MIC and up to 3 dilutions above the MIC were be sampled and plated to determine viable bacteria. Ten microliter aliquots were spotted in duplicate for each concentration/well sampled (the MIC and three wells above the MIC). The MBC was determined based on a pre-determined threshold which indicates a 99.9% decrease in viable bacteria post-incubation relative to the inoculum.

RESULTS AND DISCUSSION

As detailed in the table below CBD and THC exhibit antimicrobial activity and are overall biocidal against the strains tested.

| | THC | | | CBD | | |
|---|---|---|---|---|---|---|
| Organism | MIC | MBC | MBC:MIC[3] | MIC | MBC | MBC:MIC |
| S. aureus ATCC 29213 | 4 | 4 | 1 | 1 | 2 | 2 |
| S. aureus MMX 757 | 4 | 32 | 8 | 1 | 1 | 1 |
| E. faecalis ATCC 29212 | 2 | 8 | 4 | 2 | 2 | 1 |
| E. faecalis MMX 848 | 2 | 4 | 2 | 1 | 2 | 2 |
| S. pneumoniae ATCC 49619 | 1 | ID | NA | 1 | 4 | 4 |
| S. pyogenes MMX 404 | 32 | 32 | 1 | 32 | 32 | 1 |
| E. coli ATCC 25922 | >256 | NT | NA | >256 | NT | NA |
| C. difficile ATCC 700057 | 64 | 128 | 2 | 16 | 32 | 2 |
| C. difficile MMX 8330 | 64 | 64 | 1 | 32 | 32 | 1 |
| C. difficile MMX 8333 | 64 | 128 | 2 | 16 | 32 | 2 |
| B. bifidum MMX 3965 | 32 | 128 | 4 | 16 | 32 | 2 |
| B. longum MMX 3968 | 32 | >256 | >8 | 16 | 64 | 4 |
| B. fragilis ATCC 25285 | >256 | NT | NA | 16 | NT | NA |

ID: indeterminate,
NT: not tested,
NA: not applicable
[1]CLSI QC range shown in parenthesis
[3]MBC:MIC ratios of 1-4 are indicative of bactericidal activity.

| | Control Agents | | | | | |
|---|---|---|---|---|---|---|
| | Imipenem | | | Metronidazole | | |
| Organism | MIC | MBC | MBC:MIC | MIC | MBC | MBC:MIC |
| S. aureus ATCC 29213 | 0.015 (0.015-0.06)[1] | NA | NA | NT | NA | NA |

-continued

| | Control Agents | | | | | |
|---|---|---|---|---|---|---|
| | Imipenem | | | Metronidazole | | |
| Organism | MIC | MBC | MBC:MIC | MIC | MBC | MBC:MIC |
| S. aureus MMX 757 | 4 | NA | NA | NT | NA | NA |
| E. faecalis ATCC 29212 | 0.5 $(0.5-2)^1$ | NA | NA | NT | NA | NA |
| E. faecalis MMX 848 | 1 | NA | NA | NT | NA | NA |
| S. pneumoniae ATCC 49619 | 0.015 $(0.03-0.12)^1$ | NA | NA | NT | NA | NA |
| S. pyogenes MMX 404 | ≤0.008 | NA | NA | NT | NA | NA |
| E. coli ATCC 25922 | 0.12 $(0.06-0.25)^1$ | 0.12 $(0.12-0.5)^1$ | 1 | NT | NA | NA |
| C. difficile ATCC 700057 | NT | NA | NA | 0.12 | NA | NA |
| C. difficile MMX 8330 | NT | NA | NA | 0.5 | NA | NA |
| C. difficile MMX 8333 | NT | NA | NA | 0.5 | NA | NA |
| B. bifidum MMX 3965 | NT | NA | NA | 1 | NA | NA |
| B. longum MMX 3968 | NT | NA | NA | 8 | NA | NA |
| B. fragilis ATCC 25285 | NT | NA | NA | 0.5 $(0.25-2)^1$ | NA | NA |

ID: indeterminate,
NT: not tested,
NA: not applicable
$^1$CLSI QC range shown in parenthesis
$^3$MBC:MIC ratios of 1-4 are indicative of bactericidal activity.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

REFERENCES

1.) Clinical Laboratory and Standards Institute. *Methods for Dilution Antimicrobial Susceptibility Tests for Bacteria That Grow Aerobically; Approved Standard—Ninth Edition.* CLSI document M07-A10 [ISBN 1-56238-783-9]. CLSI, 950 West Valley Road, Suite 2500, Wayne, Pennsylvania 19087 USA, 2015.

2.) CLSI. *Performance Standards for Antimicrobial Susceptibility Testing; Twenty-Seventh Informational Supplement.* CLSI document M100-S27. CLSI, 940 West Valley Road, Suite 1400, Wayne, Pennsylvania 19087-1898 USA, 2017.

3.) CLSI. *Methods for Antimicrobial Susceptibility Testing of Anaerobic Bacteria; Approved Standard—Seventh Edition.* CLSI document M11-A7 (ISBN 1-56238-626-3). CLSI, 940 West Valley Road, Suite 1400, Wayne, Pennsylvania 19087-1898 USA, 2007.

4.) CLSI. *Reference Method for Broth Dilution Antifungal Susceptibility Testing of Yeasts; Approved Standard—Third Edition.* CLSI document M27-A3 [ISBN 1-56238-666-2]. CLSI, 940 West Valley Road, Suite 1400, Wayne, Pennsylvania 19087-1898 USA, 2008.

5.) CLSI. *Reference Method for Broth Dilution Antifungal Susceptibility Testing of Filamentous Fungi; Approved Standard—Second Edition.* CLSI document M38-A2 [ISBN 1-56238-668-9]. CLSI, 940 West Valley Road, Suite 1400, Wayne, Pennsylvania 19087-1898 USA, 2008.

6.) CLSI. *Reference Method for Broth Dilution Antifungal Susceptibility Testing of Yeasts; Fourth Informational Supplement.* CLSI document M27-S4. CLSI, 940 West Valley Road, Suite 1400, Wayne, Pennsylvania 19087-1898 USA, 2012.

7.) Ali, E. M. M., et al. (2012). Antimicrobial Activity of *Cannabis sativa* L. Chinese Medicine. 3:61-64.

8.) Appendino, G., et al. (2008). Antibacterial Cannabinoids from *Cannabis sativa*: A Structure-Activity Study. J Nat Prod. 71(8): 1427-1430.

9.) CDC (2013). Antibiotic/Antimicrobial Resistance: Biggest Threats. Accessed on 2017 May 8: https://www.cdc.gov/drugresistance/biggest_threats.html 10.) CDC. (2015). Nearly half a million Americans suffered from *Clostridium difficile* infections in a single year. Press release. Accessed on 2017 May 8: https://www.cdc.gov/media/releases/2015/p0225-*clostridium-difficile*.html 11.) Gigli, S., et al. (2017). Cannabidiol restores intestinal barrier dysfunction and inhibits the apoptotic process induced by *Clostridium difficile* toxin A in Caco-2 cells. United European Gastroenterology J. 0(0): 1-8.

12.) Kabelik, J. et al. (1960). *Cannabis* as a medicament. UN Office on Drugs and Crime. Accessed on 20170508: https://www.unodc.org/unodc/en/data-and-analysis/bulletin/bulletin_1960-01-01_3_page003.html 13.) van Klingeren, B., Ten Ham, M. (1976). Antibacterial activity of (delta9)-tetrahydrocannabinol and cannabidiol. Antonie van Leeuwenhoek. 42(1976): 9-12.

14.) WHO. (2014). Antimicrobial Resistance, Global Report on Surveillance.
15.) WHO. (2017). Global priority list of antibiotic-resistant bacteria to guide research, discovery, and development of new antibiotics. Accessed on 20170508: http://www.who.int/medicines/publications/WHO-PPL-Short_Summary_25Feb-ET_NM_WHO.pgf
16.) CLSI. Methods for Determining Bactericidal Activity of Antimicrobial Agents; Approved Guideline. CLSI document M26-A. CLSI, 940 West Valley Road, Suite 1400, Wayne, Pennsylvania 19087-1898 USA, 1999.

What is claimed:

1. A composition having antimicrobial activity comprising: at least one cannabinoid prodrug selected from a cannabidiol prodrug that is metabolized to cannabidiol, a tetrahydrocannabinol prodrug that is metabolized to tetrahydrocannabinol, or combinations thereof; and at least one pharmaceutical carrier or excipient, wherein said antimicrobial activity is against an *E. faecalis* infection, a *S. pneumonia* infection, a *C. difficile* infection, a *L. crispatus* infection, a *B. bifidum* infection, a *B. longum* infection, or combinations thereof.

2. The composition of claim 1, wherein the cannabinoid prodrug is a cannabidiol prodrug that is metabolized to cannabidiol.

3. The composition of claim 2, wherein said antimicrobial activity is against an *E. faecalis* infection.

4. The composition of claim 3, wherein said composition is formulated for oral administration.

5. The composition of claim 3, wherein said composition is formulated for topical administration.

6. The composition of claim 2, wherein the antimicrobial activity is against a *C. difficile* infection.

7. The composition of claim 6, wherein said composition is formulated for oral administration.

8. The composition of claim 6, wherein said composition is formulated for topical administration.

9. The composition of claim 1, wherein said composition is formulated for oral administration.

10. The composition of claim 1, wherein said composition is formulated for topical administration.

11. The composition of claim 1, wherein the cannabinoid prodrug is a tetrahydrocannabinol prodrug that is metabolized to tetrahydrocannabinol.

12. The composition of claim 11, wherein the antimicrobial activity is against a *C. difficile* infection.

13. The composition of claim 12, wherein said composition is formulated for oral administration.

14. The composition of claim 12, wherein said composition is formulated for topical administration.

15. The composition of claim 11, wherein the antimicrobial activity is against an *E. faecalis* infection.

16. The composition of claim 15, wherein said composition is formulated for oral administration.

17. The composition of claim 15, wherein said composition is formulated for topical administration.

18. The composition of claim 1, wherein said composition comprises a further active ingredient selected from other cannabinoid compounds, other antimicrobial agents, anti-inflammatory agents, probiotics, or combinations thereof.

19. The composition of claim 1, wherein said composition is formulated for delivering the cannabinoid prodrug to the gastrointestinal tract.

20. The composition of claim 1, wherein said composition is said antimicrobial activity is against an *S. pneumonia* infection, a *L. crispatus* infection, a *B. bifidum* infection, a *B. longum* infection, or combinations thereof.

* * * * *